United States Patent [19]

Chlebowski et al.

[11] Patent Number: 4,656,128
[45] Date of Patent: Apr. 7, 1987

[54] MODIFIED ALKALINE PHOSPHATASE

[75] Inventors: Jan F. Chlebowski; Catherine H. Roberts, both of Richmond, Va.

[73] Assignee: Research Corporation, New York, N.Y.

[21] Appl. No.: 724,750

[22] Filed: Apr. 18, 1985

Related U.S. Application Data

[63] Continuation-in-part of Ser. No. 692,969, Jan. 21, 1985.

[51] Int. Cl.$^4$ .................. G01N 33/54; C12Q 1/42; C12Q 21/00; C12P 19/30; C12P 19/32; C12R 1/19
[52] U.S. Cl. ............................ 435/7; 435/21; 435/68; 435/89; 435/92; 435/849
[58] Field of Search .................. 435/7, 68, 89, 92, 196

[56] References Cited

PUBLICATIONS

Jemmerson et al., FEBS Letters, vol. 173, No. 2, pp. 357–359 (Aug. 1984).

*Primary Examiner*—Lionel M. Shapiro
*Attorney, Agent, or Firm*—Scully, Scott, Murphy & Presser

[57] ABSTRACT

This invention provides a proteolytically modified alkaline phosphatase which is irreversibly inactivated upon removal of divalent ions. The modified enzyme is particularly useful as a molecular biological or immunological reagent.

14 Claims, 14 Drawing Figures

H₂N(R) T P E M P V L E N R A A Q G D I T A P G G
                    10  ↑
⁴⁴⁰Y T M K A A L G L K^COO⁻

═ sequence determined by manual Edman degradation
─ sequence determined by automated Edman degradation

FIG. 4

MODIFIED ALKALINE PHOSPHATASE

This invention was made in part with support from the National Institute of Health Grant GM27493-05 and Institute of Biotechnology, Center for Innovative Technology (VA) Grant B10-5004.

This application is a continuation-in-part of U.S. patent application Ser. No. 692,696 filed Jan. 21, 1985.

FIELD OF THE INVENTION

This invention relates to the field of enzymology. More specifically, this invention relates to a modified alkaline phosphatase which is particularly useful in various molecular biological and immunological protocols where the alkaline phosphatase enzyme is required.

BACKGROUND OF THE INVENTION

Alkaline phosphatase (orthrophosphoric-monoester phosphohydrolase, alkaline optimum, EC. 3.1.3.1) is an enzyme widely distributed in nature. The enzyme has been isolated from a variety of eukaryotic sources such as human placenta, liver, bone, leukocytes and serum; bovine bone, intestine (particularly calf intestinal) and kidney; and rat liver; as well as a variety of prokaryotic sources including *Escherichia coli, Bacillus subtilis, Bacillus, lichenoformis, Micrococcus sodonensis, Thermoactinomyces, vulgaris,* and *Lysobacter enzymogenes.*

The enzymes have been reasonably well characterized and all appear to be Zn(II) metalloenzymes which catalyze the hydrolysis of monoesters by means of the formation of a phosphoseryl intermediate. A number of excellent literature reviews exist (See for example: Reid, T. W. and I. B. Wilson, Enzymes 4: 737 (1971); Coleman, J. E. and J. F. Chlebowski, *Adv. Inorg. Biochem.* 1:1 (1979); McComb, R. B. et al. "Alkaline Phosphatase", Plenum Press, New York, (1979); Coleman, J. E. and P. Gettins, *Adv. in Enzymol.* 55: 381 (1983); and Wyckoff, H. W. et al., *Adv. in Enzmol.* 55: 453 (1983)).

The enzyme from *E. coli* has been particularly well studied and complete amino acid sequence as well as three dimensional structural data are available. The enzyme exists as a dimer of approximately 94,000 molecular weight, composed of two identical approximately 47,000 molecular weight monomer subunits. The monomer is an unglycosylated single chain of 449 amino acids in its mature form. The enzyme is localized in the periplasmic space and as is common with such extra-membrane protein products, it is initially synthesized on membrane bound polysomes in a precursor form and secreted through the membrane with the assistance of a signal peptide region which is cleared from the enzyme as a consequence of its deposition within the periplasmic region.

In its native form, the protein possesses remarkable stability as reflected by its resistance to thermal and chemical denaturation (Chlebowski, J. F., et al., *J. Biol. Chem.* 252: 7053 (1977)). The enzyme has also previously been reported to be resistant to proteolytic modification (Schlesinger, M. J. et al. *Ann. N.Y. Acad. Sci.* 166: 368 (1969); Reid I M and I. B. Wilson, *The Enzymes* 4: 373 (1971). Stabilization of the protein is due principally to the association of Zn(II) and Mg(II) ions in the holoenzyme. As isolated from the periplasmic space of the *E. coli* bacterium, the enzyme has bound up to 4 eq of Zn(II) and 2 eq of Mg(II). Three metal ion-binding sites, designated A, B, and C, are located on each subunit in a cluster, lying within 4 to 7 Å° of one another. Since the binding of a minimum of 2 eq of Zn(II)/dimer is required for activity (phosphate monoester hydrolysis), the metal ion cluster appears to define the active site region. The location of Ser-102, which is covalently phosphorylated in the course of the reaction, at the metal ion cluster permits an unequivocal location of the active center.

The protein is reported to display cooperative subunit interactions affecting metal ion association with the metal-free apoenzyme and ligand association with the active metalloenzyme. Since the active centers of the holoenzyme lie 32 Å° apart across the 2-fold symmetry axis relating the subunits of the dimer, such cooperative effects would appear to involve the transmission of conformational information through the interconnecting polypeptide structure. Consistent with this depiction is the extensive array of intersubunit contacts at the monomer-monomer interface. The existence of cooperative phenomena has, however, been a source of continuous controversy in the literature. This has, at least in part, detracted from the plausibility of allosteric interactions as playing a role in modulating the structure and reactivity of the enzyme.

As mentioned above, the effects of certain ions on the stability of the enzyme have been studied in some detail not only with respect to the *E. coli* enzyme but also with respect to a number of different alkaline phosphatases isolated from a variety of sources.

Ensinger, et al. (*Biochem. et Biophys. Acta.* 527: 432 (1978)) discloses the inactivation of calf intestine alkaline phosphatase by chelating agents. The inactivation was shown to be reversible (i.e., the activity was restored by readdition of $Zn^{++}$) at pH 8.0. It was also shown that, at more alkaline pHs, the inactivation became irreversible and that complete irreversible inactivation occurred at pH 9.8.

In an investigation of structural-functional domains of bacterial alkaline phosphatase, McCracken and Meighen (*J. Biol. Chem.* 256 (8): 3945 (1981)) provide evidence that certain histidine residues are responsible for meta ion binding and that by chemically blocking (derivatizing) the histidine moieties, the stability of the enzyme subunit structure is affected.

Sinha et al. (*Indian J. Exp. Biol.* 19: 453 (1981)) disclose the cation requirements of an alkaline phosphatase from a thermophile, *Thermoactinomyces vulgaris.* These researchers demonstrate that the presence of $Mg^{++}$ is necessary.

Ueda (*Biol. J. Clin. Pathol.* 80(3): 342 (1983)) discloses certain physiocochemical properties of an alkaline phosphatase isolated from leukocytes. The enzyme is relatively heat labile, being 100% inactivated at 56° C. after 2 minutes whereas the placental form of alkaline phosphatase is 100% stable at the same temperature after 15 minutes. The leukocyte alkaline phosphatase is inhibited by 50% after incubation with 0.02M EDTA.

Yamashita, et al. (*J. Biochem.* (JAPAN) 80: 129 (1976) teach that tryptic digestion of serum protects human serum alkaline phosphatase from histidine-mediated heat inactivation. The authors show that trypsin does not affect the heat stability of alkaline phosphatase in the absence of histidine.

In a recent report vonTigerstrom (*Appl. and Environ. Microbiol.* 47 (4): 693 (1984)) discloses a potential new source of alkaline phosphatase. One of the forms of the enzyme is apparently extracellular. The Lysobacter enzyme can be distinguished from other bacterial alkaline phosphatases and calf intestine alkaline phosphatases in that chelating agents have little or no effect.

In direct contrast to the reports of Schlesinger et al. (supra) and Yamashita et al. (supra), it has now been surprisingly discovered that the alkaline phosphatase from *E. coli* is susceptibile to modification by trypsin. It is further demonstrated that the modified enzyme displays unique properties that render the modified enzyme particularly useful in a variety of enzymological procedures.

BRIEF DESCRIPTION OF THE INVENTION

This invention provides a proteolytically modified alkaline phosphatase.

In a further embodiment this invention provides a trypsin modified bacterial alkaline phosphatase characterized in having 10 or 11 amino acids deleted from the $NH_2$ terminal region thereof when compared to the native unmodified enzyme, capable of expressing dephosphorylating activity of up to about 80% of the native unmodified enzyme and capable of substantially total irreversible inactivation upon removal of divalent ions.

In a further embodiment this invention provides a process for the production of a proteolytically modified alkaline phosphatase comprising contacting a native alkaline phosphatase with a proteolytic enzyme in a reaction mixture under conditions of time and temperature sufficient to result in the removal of an $NH_2$ terminal fragment.

In a further embodiment this invention provides a method for enzymatically dephosphorylating the 5' phosphate groups of nucelic acids, the improvement which comprises contacting the nucelic acid to be dephosphorylated under dephosphorylating conditions with a proteolytically modified alkaline phosphatase.

In a further embodiment this invention provides a method for the detection of an immunological reaction by an enzyme linked immunoassay. The improvement consisting of employing a modified alkaline phosphatase as an enzymatic detection means.

In a further embodiment this invention provides a method for the enzymatic hydrolysis of phosphate monoester. The improvement consisting of contacting said phosphate monoester under hydrolysis sufficient to release phosphate therefrom with a modified alkaline phosphate.

DETAILED DESCRIPTION OF THE DRAWINGS

Figure 1:
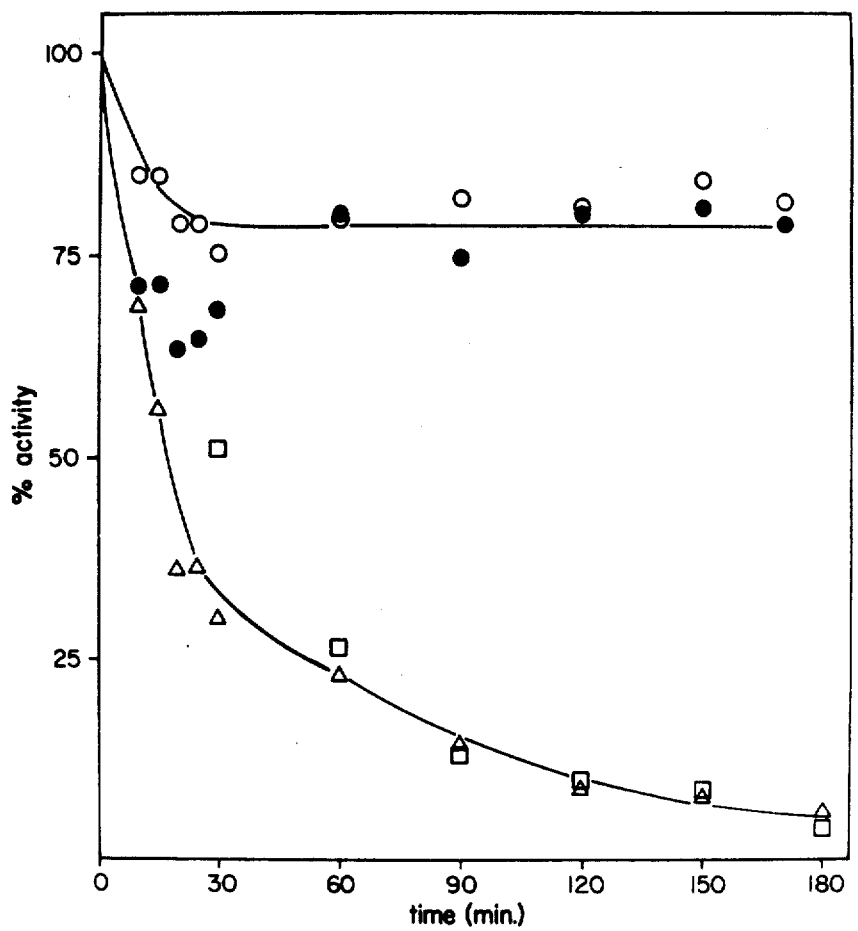

FIG. 1 illustrates the effect of 10% trypsin on the activity of apoalkaline phosphatase and native alkaline phosphatase. Conditions of trypsin incubation: 0.01M Tris, 0.01M NaOAc, 0.1M NaCl, pH 6.5 or 8.0, [alkaline phosphatase]=3 mg/ml; 10% (w/w) trypsin. Apoalkaline phosphatase, pH 6.5 (□); apoalkaline phosphatase, pH 8.0 (Δ); native alkaline phosphatase, pH 6.5 (O); native alkaline phosphatase ph 8.0 (●). At the indicated time points, 5 μl of enzyme were removed and assayed as described under "Materials and Methods" in Example I. Native enzyme samples were at saturating concentrations of Zn(II) and Mg(II) ($5 \times 10^{-5}$M $ZnCl_2$ and 10 mM $MgCl_2$).

Figure 2:
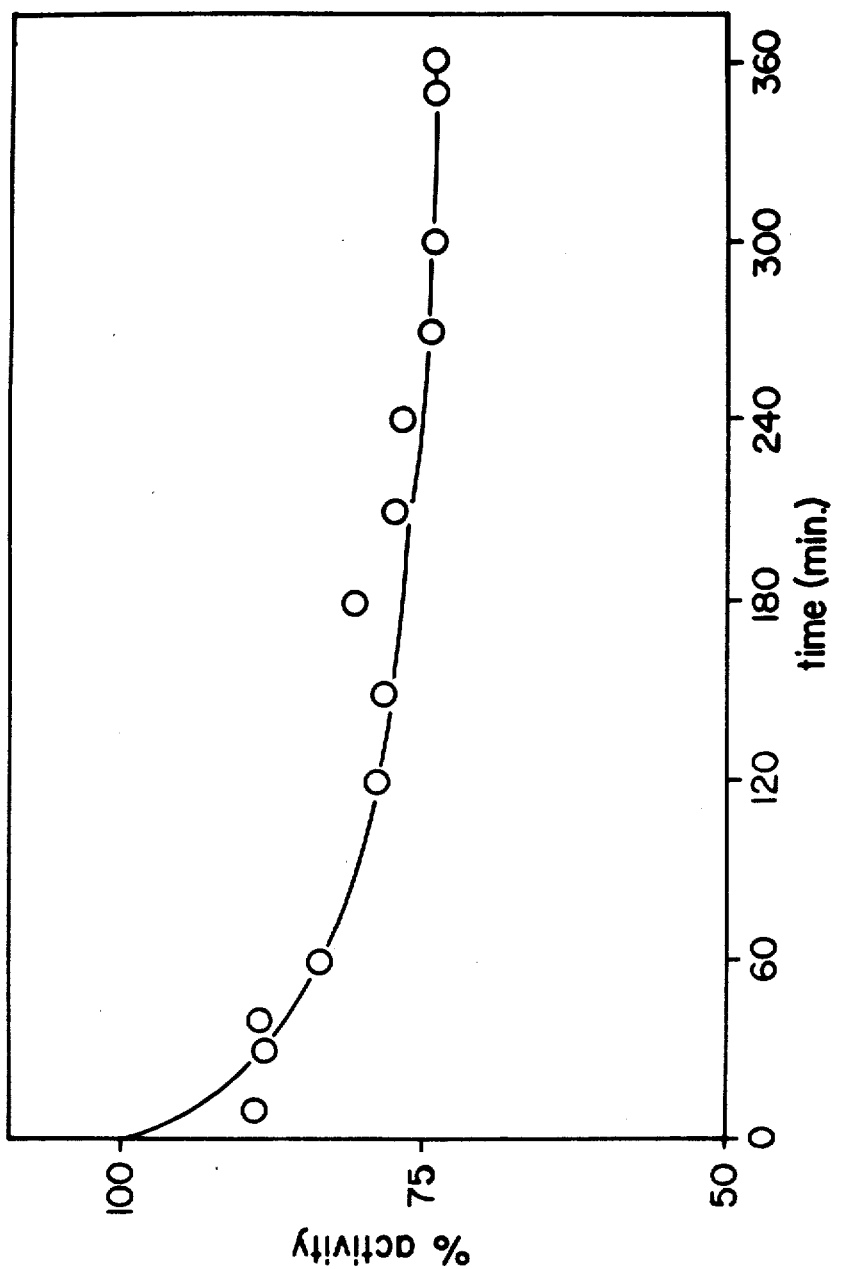

FIG. 2 illustrates the effect of 1% trypsin on the activity of native alkaline phosphatase. Conditions of trypsin incubation: 0.01M Tris, 0.01m NaOAc, 0.1M NaCl, $5 \times 10^{-5}$M $ZnCl_2$, 10 mM $MgCl_2$, ph 8.0, [alkaline phosphatase]=3 mg/ml, 1% (w/w) trypsin. At the indicated time points, 5 μl of enzyme were removed and assayed as described under "Materials and Methods" in Example I.

Figure 3:
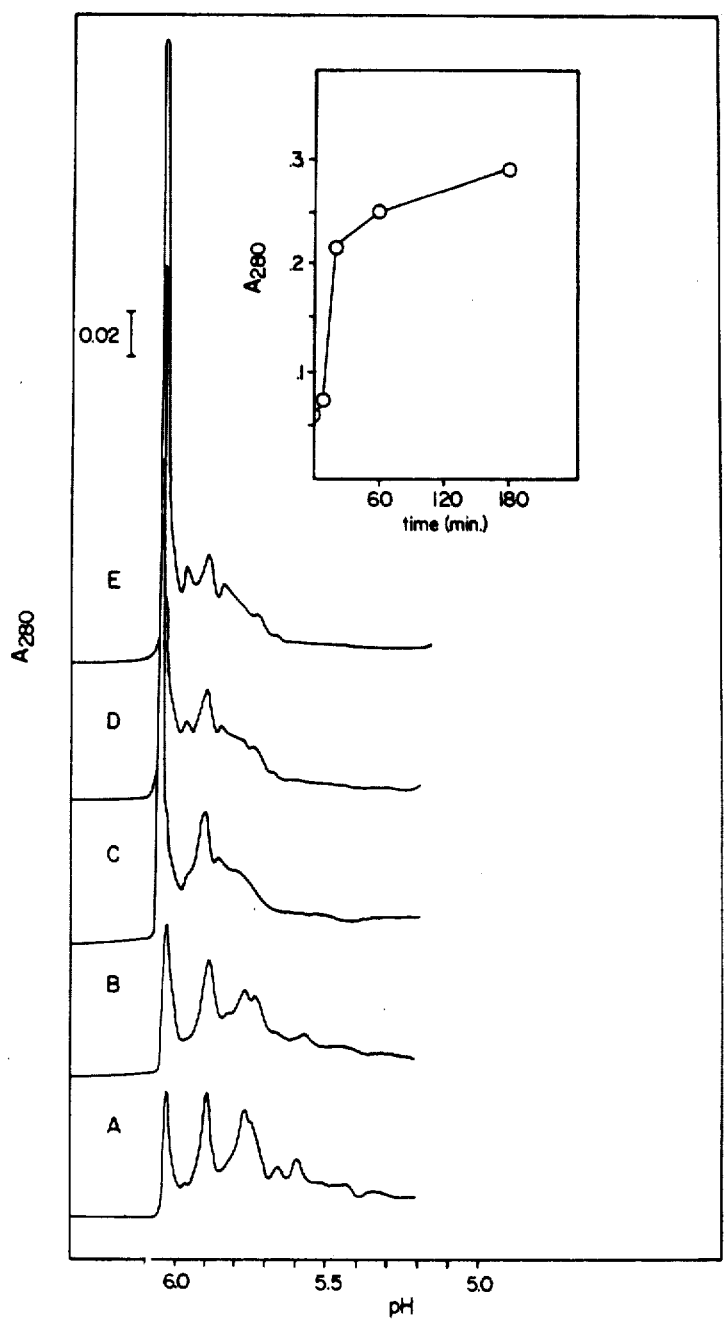

FIG. 3 illustrates the chromatofocusing of native and trypsin-treated alkaline phosphatase. Conditions of trypsin incubation: 0.025M Bis-Tris-HCl, pH 6.7, [alkaline phosphatase]=3 mg/ml, 1% (w/w) trypsin. Time of trypsin incubation (A) 0 min, (B) 10 min, (C) 20 min, (D) 60 min, (E) 180 min. 0.5-mg samples were removed at each time point and analyzed using chromatofocusing. Chromatofocusing was performed as described under "Materials and Methods" in Example I.

FIG. 4 illustrates the results of the sequence determinations of the trypsin modified alkaline phosphatase.

Figure 5:
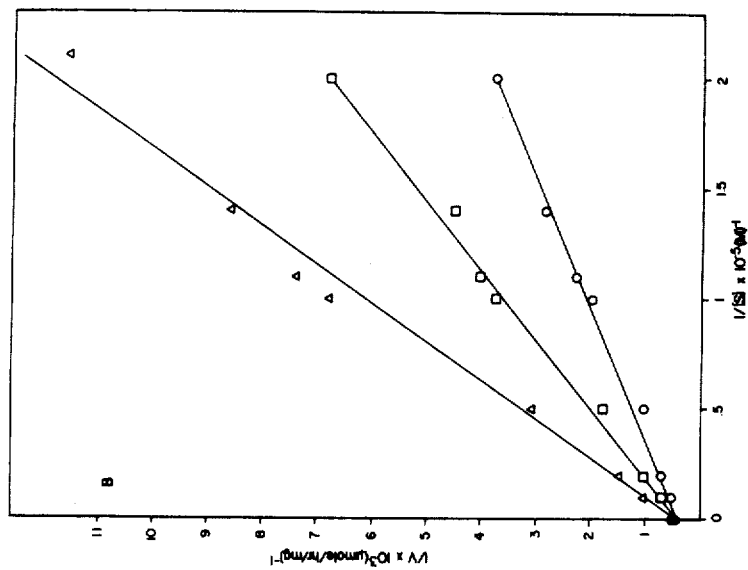
Figure 5:
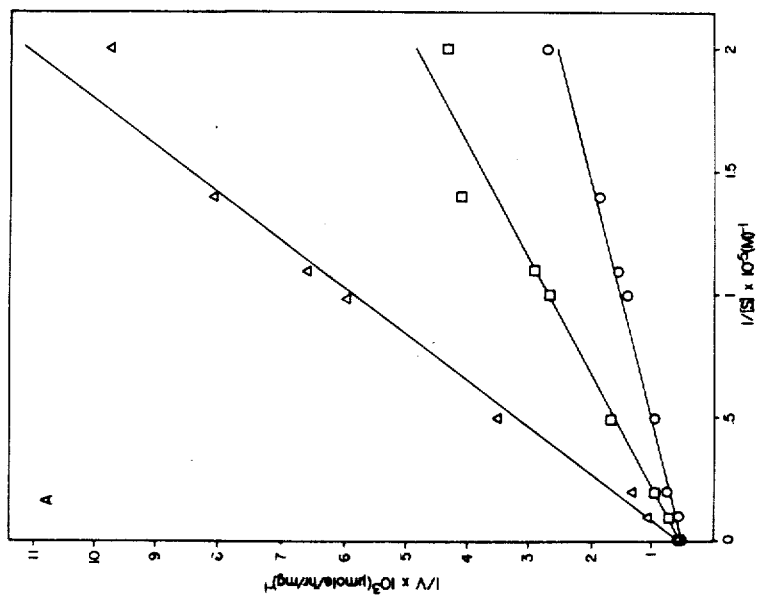

FIG. 5 illustrates the determination of kinetic constants for native alkaline phosphatase and trypsin-modified alkaline phosphatase. A, trypsin-modified alkaline phosphatase, $[K_2HPO_4]=0$ (0), $1 \times 10^{-5}$M (□), $3 \times 10^{-5}$M (Δ). B, Native alkaline phosphatase, $[K_2HPO_4]=0$ (0), $1 \times 10^{-5}$M (□), $3 \times 10^{-5}$M (Δ). The enzyme was assayed as described under "Materials and Methods" in Example I except that the assay solution contained $K_2HPO_4$ at the indicated concentration and PNPP at concentrations ranging from $5 \times 10^{-6}$ to $1 \times 10^{-3}$M.

Figure 6:
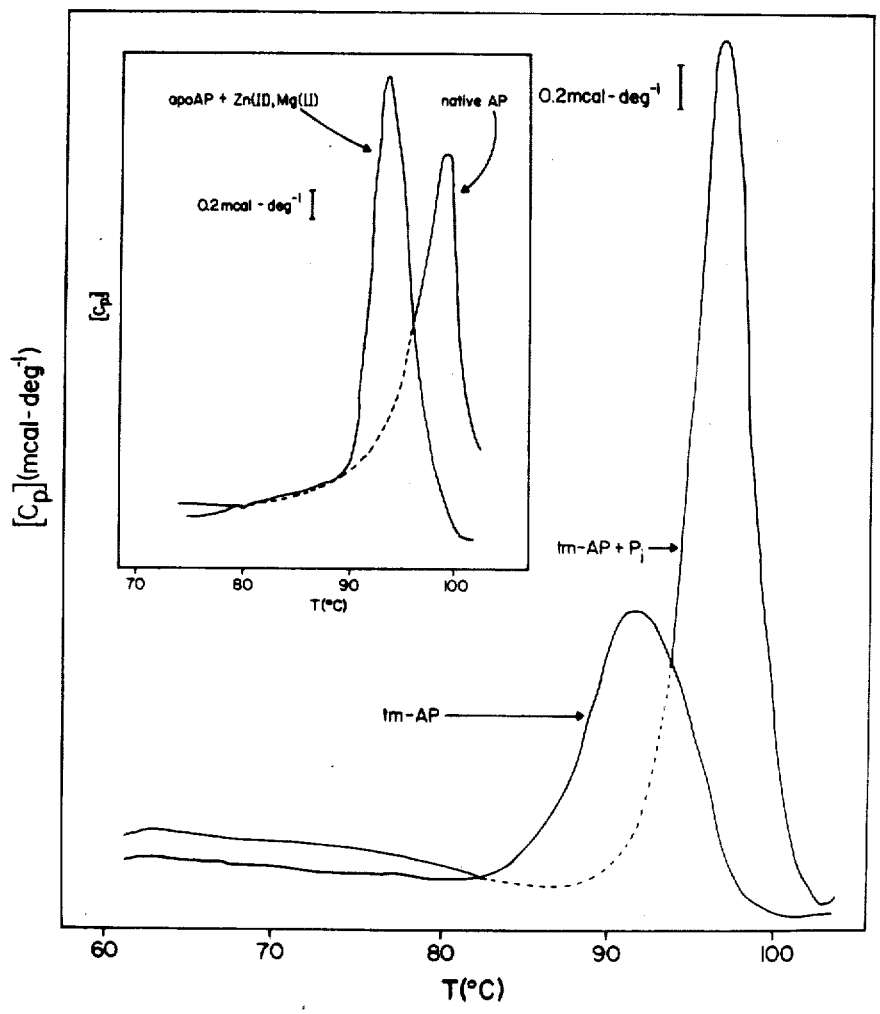

FIG. 6 illustrates the DSC (differential scanning calorimetry) of trypsin-modified alkaline phosphatase and native alkaline phosphatase. Conditions: 0.01M Tris, 0.01M NaOAc, 0.1M NaCl, pH 8.0, $5 \times 10^{-5}$M $ZnCl_2$, 10 mM $MgCl_2$. Two equivalents of inorganic phosphate were added to the sample for the scan labeled tm-AP+Pi. It was assumed that apoalkaline phosphatase (apoAP) plus saturating amounts of Zn(II) and Mg(II) closely approximates the native enzyme without $P_i$ bound. DSC was performed as described under "Materials and Methods" of Example I tm-AP, trypsin-modified alkaline phosphatase.

Figure 7:
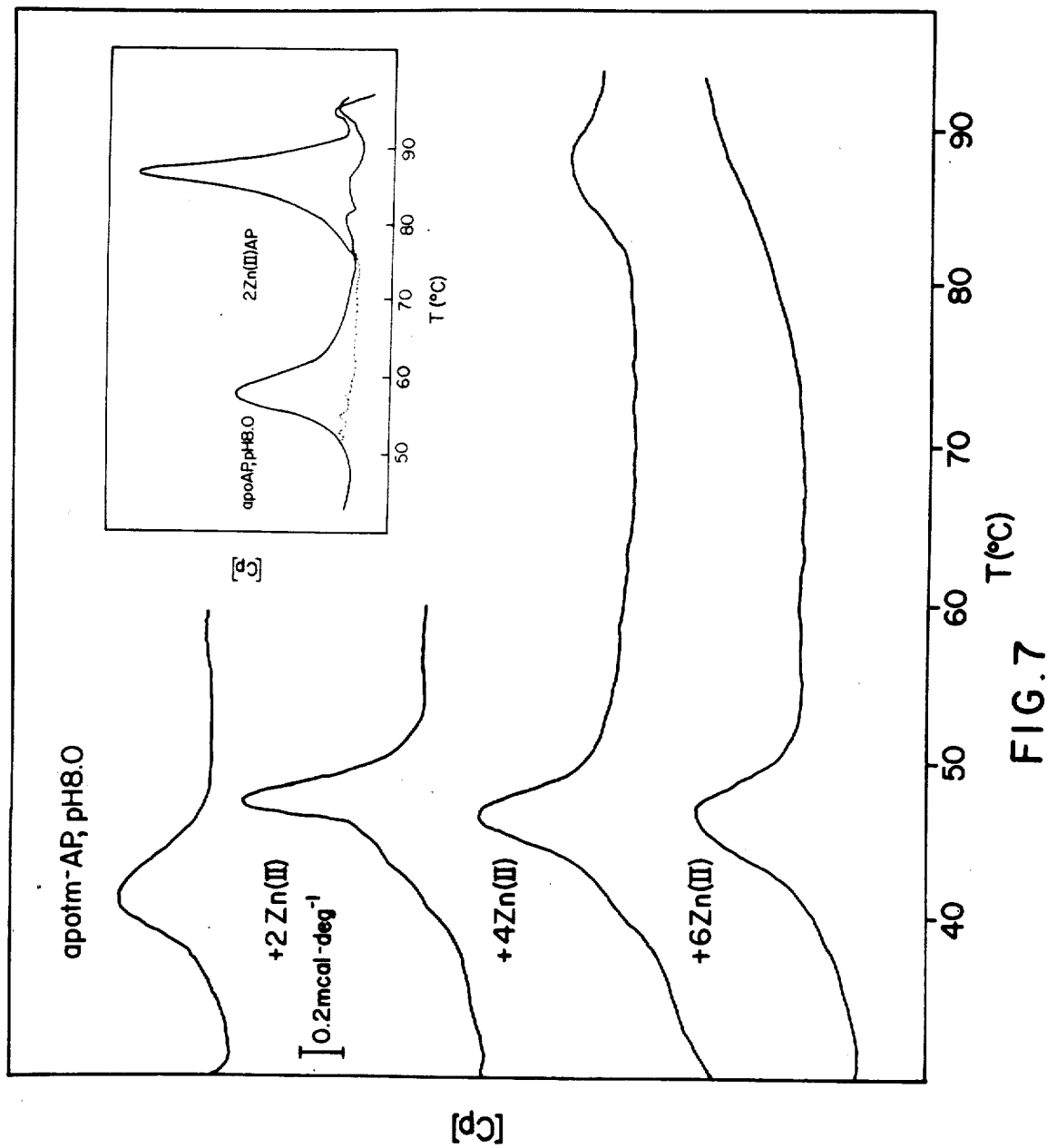

FIG. 7 illustrates the effect of Zn(II) addition to apo trypsin-modified alkaline phosphatase and apo alkaline phosphatase. Conditions: 0.01M Tris, 0.01M NaOAc, 0.1M NaCl, pH 8.0; [alkaline phosphatase]-2 mg $ml^{-1}$. Aliquots of a concentrated stock solution of Zn(II) $SO_4$ were added to the protein solution to yield the indicated equivalents of Zn(II). Calorimetric scans were performed immediately after metal ion addition. For details see "Materials and Methods" of Example V.

Figure 8:
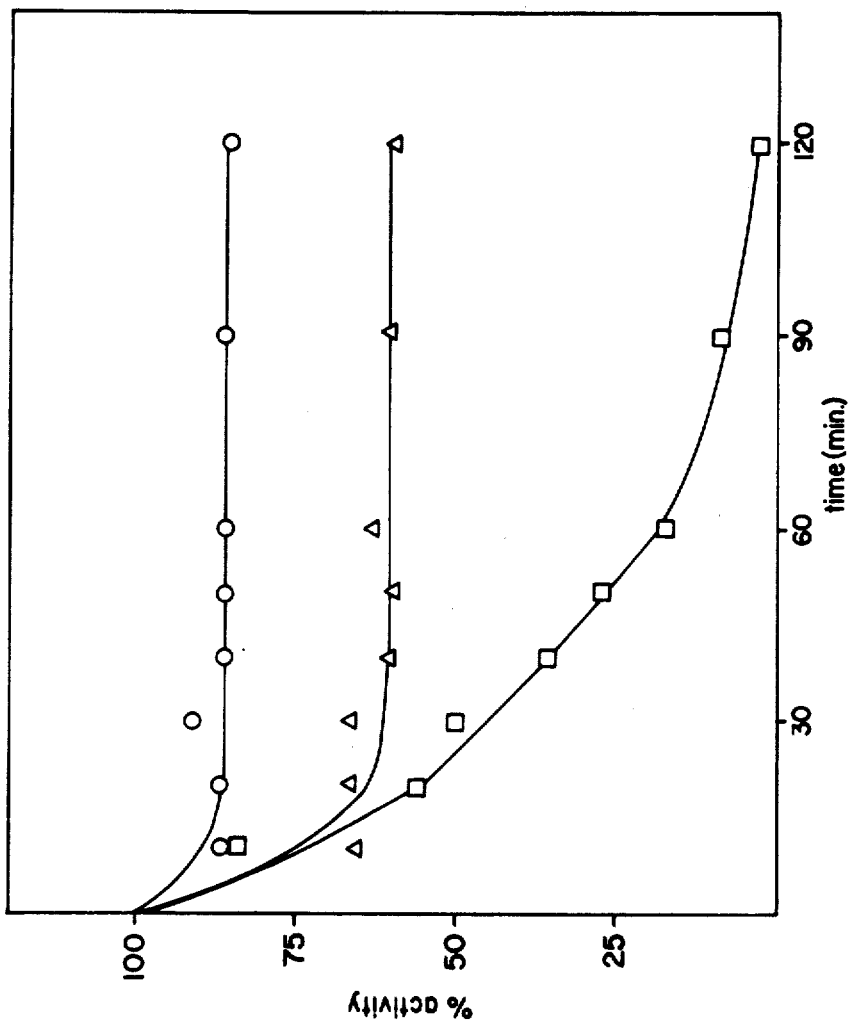

FIG. 8 illustrates the effect of 10% trypsin on the activity of apoalkaline phosphatase, native alkaline phosphatase, and $Zn(II)_2$ alkaline phosphatase. Conditions of trypsin incubation; 0.01M Tris, 0.01M NaOAc, 0.1M NaCl, pH 8.0, [alkaline phosphatase]=3 mg/ml; 10% (w/w) trypsin. Apoalkaline phosphatase (□); native alkaline phosphatases (0); $Zn(II)_2AP$ (Δ). At the indicated time points, 5 μl of enzyme were removed and assayed as described under "Materials and Methods".

Figure 9:
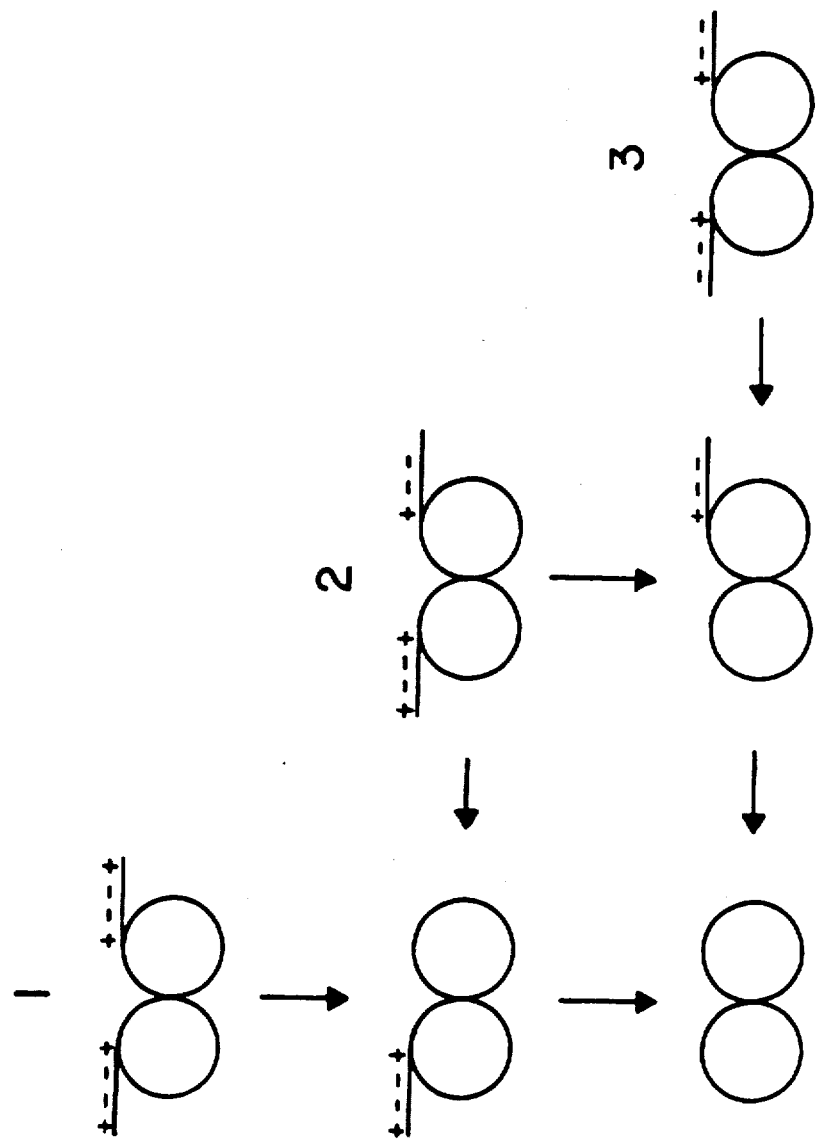

FIG. 9 illustrates net charge of the trypsin susceptible $NH_2$-terminal peptide for the isoenzymes and modified forms of alkaline phosphatase.

Figure 10:
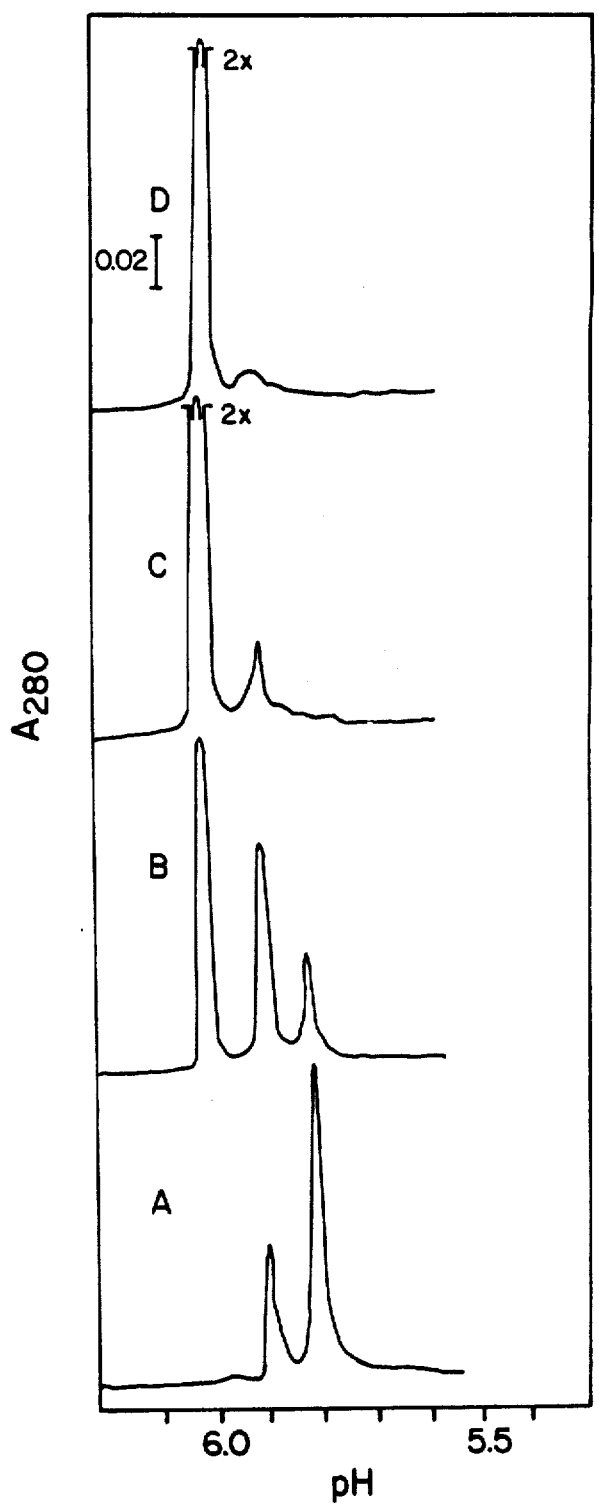

FIG. 10 illustrates the chromatofocusing of native and trypsin-treated alkaline phosphatases. Conditions of trypsin incubation: 0.025M Bis-Tris-HCl, pH 6.7, [alkaline phosphatase]=3 mg/ml, 1% (w/w) trypsin; time of exposure to the trypsin (A) 0, (b) 0.5 hour, (C) 1.5 hour, (D) 2.5 hour. 0.25 mg samples were removed at the indicated time points and analyzed using chromatofocusing as described under "Materials and Methods" above.

Figure 11:
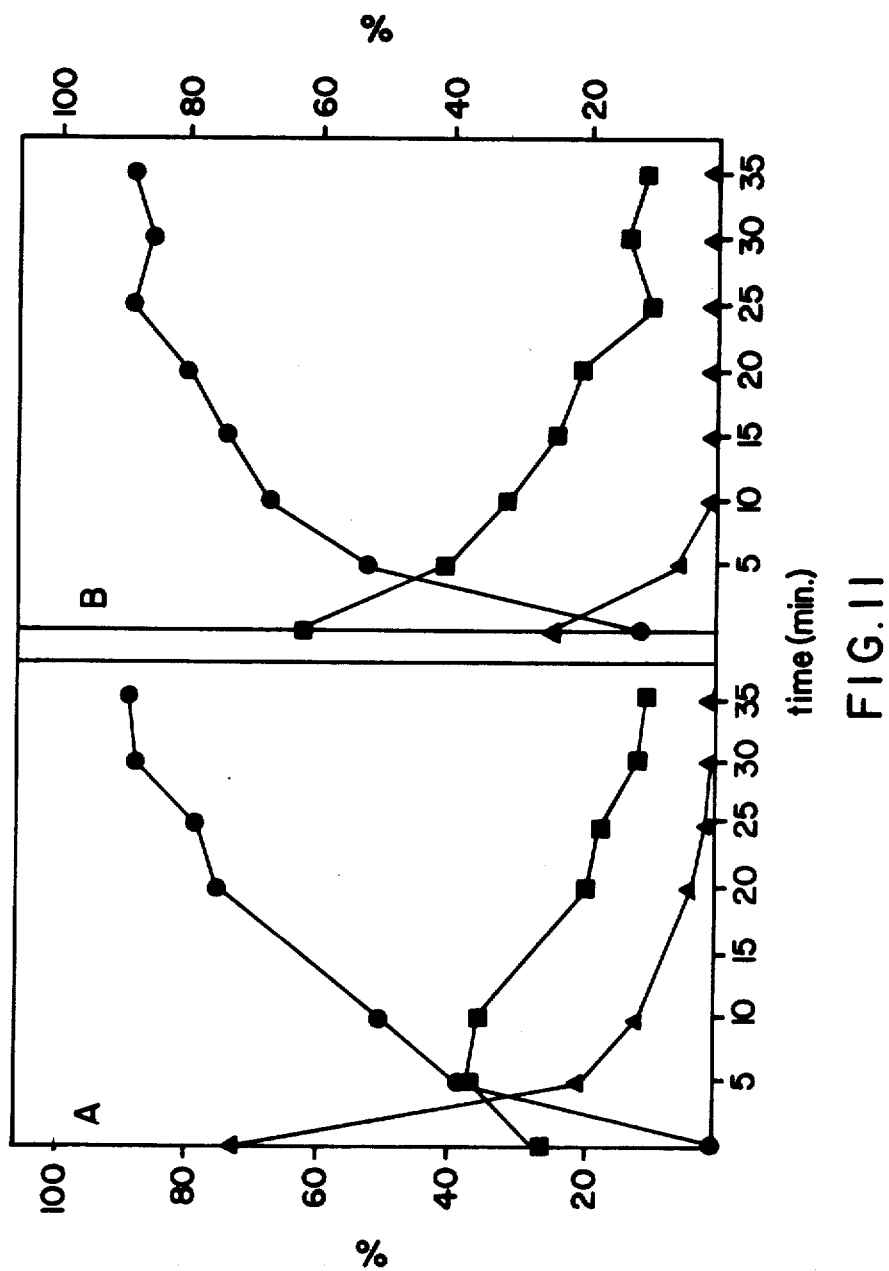

FIG. 11 illustrates a plot of percent total area vs. time of trypsin exposure. Condition: 0.025M Bis-Tris-HCl, pH 6.7, [alkaline phosphatase]=3 mg/ml, 1.6 units trypsin activity/mgAP. Samples of isozyme 3 (A) or isozyme 2 (B) were treated with trypsin. 0.25 mg samples were removed at the indicated time points and analyzed using chromatofocusing as described under "Materials and Methods". The areas of the peaks eluting at pH 6.0 (●), pH 5.9 (■), and pH 5.8 (▲) were intergrated and plotted as the percent of the total area of the three peaks.

Figure 12A:
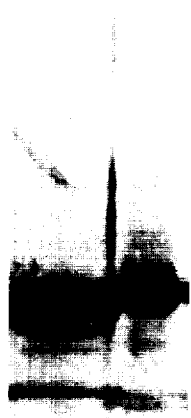
Figure 12B:

FIG. 12 depicts the polyacrylamide gel electrophoresis of native alkaline phosphatase, trypsin modified isozyme 1, and half-modified isozyme 3. 12% SDS denaturing gels were run as described under "Materials and Methods". (A) lane 1, isozyme 1 which has been treated with 10% trypsin, 4 h., pH 8.0; lane 2, native AP. (B) lane 1, native AP; lane 2, and aliquot from the peak eluting at pH 5.9 in the chromatographic elution profile, FIG. 4.

Figure 13:
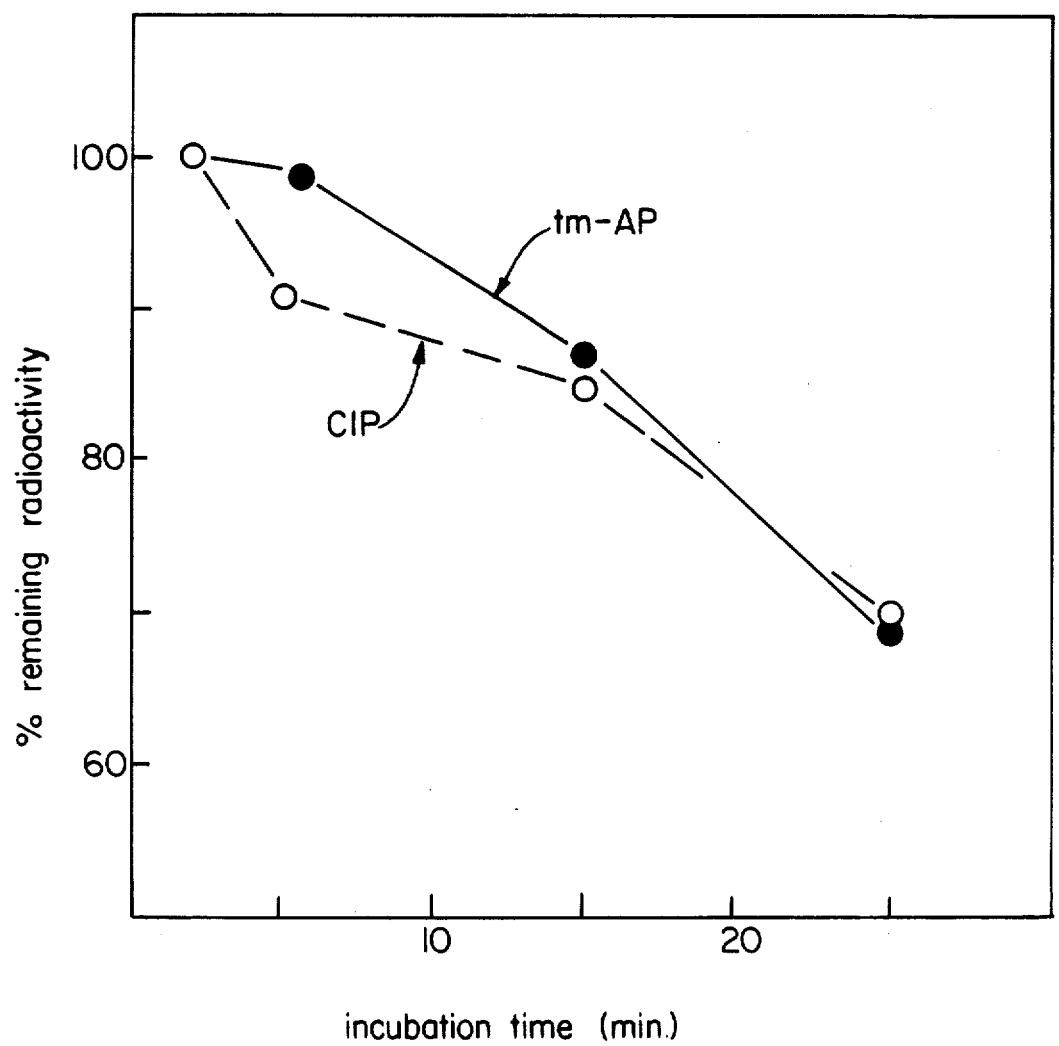

FIG. 13 illustrates the dephosphorylation of DNA by tm-AP (●) and CIP (0). $^{32}$P-labelled salmon sperm DNA was prepared as previously described (Maniatis T. et al. (surpa)). Equivalent units of CIP or tm-AP were incubated with the labelled DNA under conditions previously described for the dephosphorylation of DNA (Mainiatis T. et al. (supra)). Aliquots of 5 μl were taken at the time points indicated and added to 5 μl of 10% SDS and 10 μl 0.01M Tris, pH 8.0 buffer. Samples were extracted with phenol/chloroform and pipetted onto glass fiber filters. 100 μl cold 10% TCA was then pipetted onto filters and the filters were washed with TCA and ethanol. After drying, filters were immersed in scintillation cocktail and the radioactivity was counted. Data are shown as the percent of the initial time point radioactivity remaining at the times indicated.

Figure 14:
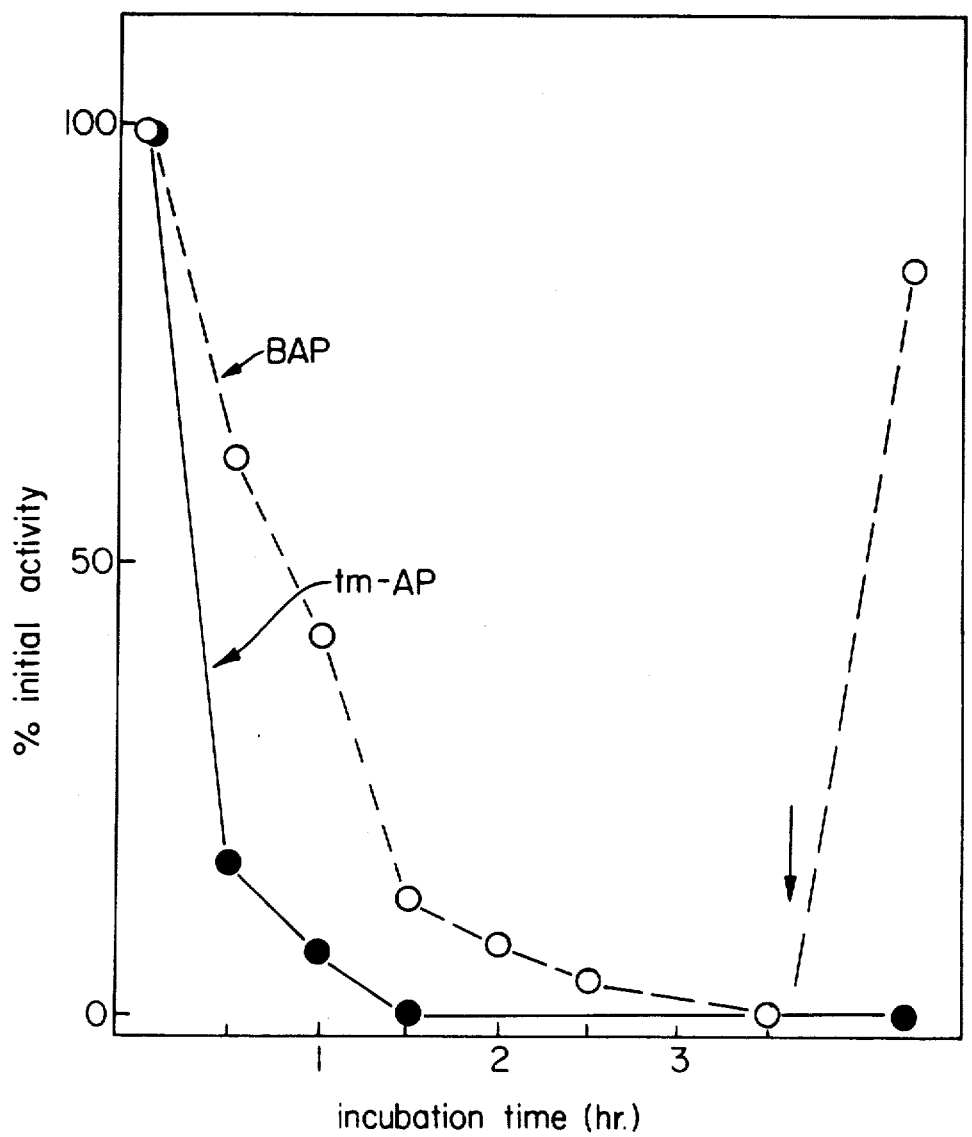

FIG. 14 illustrates the inactivation of tm-AP (●) and BAP (0) by EDTA. Enzyme was incubated with EDTA; conditions- $2.6\times10^{-6}$M enzyme, $-0.015$M EDTA, 0.5M NaCl, $5\times10^{-4}$M Mg(II), $5\times10^{-5}$M Zn(II), $5\times10^{-4}$M spermidine, 0.025M Tris, pH 7.5. Aliquots were withdrawn at the indicated time points and enzymatic activity in the standard phosphohydrolase assay (Applebury, M. L. and J. E. Coleman *J. Biol. Chem.* 244: 308 (1969)) was determined. Data are shown as the percent of the initial activity remaining at the the times indicated. Once the activity of both BAP and tm-AP had been reduced to negligible levels, the enzyme was dialyzed against 0.05M Tris, $1\times10^{-5}$M Zn(II), $1\times10^{-2}$M Mg(II), pH 8.0 (2×2L, 36 hr). Enzyme was harvested and activity determined.

DETAILED DESCRIPTION OF THE INVENTION

When employing an enzyme as a reagent in a molecular biological or immunological procedure, the ability to control the activity of the enzyme becomes of prime importance. This is particularly true in multi-step procedures where it is required that the enzyme only be active in one of the steps but not in subsequent ones. Hence, the ability to effectively and completely inactivate the enzyme is a major consideration when selecting a particular enzyme for the enzymological protocol under consideration.

An enzyme which has found widespread use in molecular biological as well as immunological procedures is alkaline phosphatase. Although not meant to be exhaustive, some of the procedures in which the use of alkaline phosphatase is important include (1) the removal of 5' phosphates from DNA or RNA prior to labelling the 5' end with $^{32}$P; (2) the removal of 5' phosphates from DNA fragments to prevent self-ligation; (3) the removal of 5' phosphate from RNAs in sequencing protocols; (4) as a reagent in an enzyme linked immunosorbent assay (ELISA); (5) as a reagent to detect the level of protein phosphorylation and (6) as a reagent to discriminate between phosphate monoester and phosphate diester linkages. In the discussion which follows, the invention will be illustrated with reference to the use of the enzyme as a reagent in nucleic acid modification protocols; however, such a specific illustration should not be considered to limit the scope of the invention as the invention contemplates the use of the modified alkaline phosphatase described herein in a variety of protocols such as enumerated above.

By native alkaline phosphatase is meant the native alkaline phosphatase enzyme as having any signal peptide sequence, if existing, removed therefrom. In the case where the enzyme is isolated from *E. coli*, the native alkaline phosphatase refers to the enzyme as isolated from the periplasmic space and having the signal sequence removed.

By modified alkaline phosphatase is meant the native phosphatase which has been subjected to the action of a proteolytic enzyme which as a result of the action of the proteolytic enzyme a polypeptide fragment has been removed from the NH$_2$ terminus of the native enzyme. Thus any protease which modifies the enzyme in the manner described above will be useful in producing the subject invention. Although a certain decrease in the activity of the enzyme may result from the procedure as described in Example I, such a result is more than compensated for by the beneficial effect with respect to specific inactivation.

As detailed in Example I, several proteases have been determined to be effective in reducing the activity of the alkaline phosphatase and having a differential effect on apo- and native forms. When the *E. coli* enzyme is modified, the fragment released by the action of trypsin contains 10 or 11 amino acids depending upon which isozyme form of the enzyme is degraded.

The introduction of the radiolabel $^{32}$P into nucleic acids as an analytical handle is routinely, if somewhat tediously, performed in a multistep procedure in which the key steps are the enzyme mediated removal (phosphatase) and replacement (kinase) of phosphoryl groups at the 5' end of the nucleic acid polymer. Such a procedure is detailed by Maniatis, T. et al. In: "Molecular Cloning: A Laboratory Manual", Cold Spring Harbor Laboratories, (1982) at Pages 133 and 134.

Thus, this standard protocol recommends (1) heat inactivation of calf intestinal phosphatase by incubation of the reaction mixture at 68°, (2) a succession of phenol/chloroform extractions to physically extract the (supposedly inactive) enzyme from the nucleic acid coupled with (3) the suggestion that addition of a metal ion chelating agent may also be required to inactivate/destabilize the activity.

In the protocol as currently employed the dephosphorylation step calls for the repeated incubation of nucleic acid substrate with aliquots of calf intestinal alkaline phosphatase (CIP) rather than the bacterial alkaline phosphatase (BAP). This choice of reagent is based on either (a) the higher specific activity of CIP or (b) the relative ease with which CIP can be heat-inactivated. Elimination of the phosphatase activity is absolutely crucial for successful application of the succeeding kinase treatment. Selection of precise incubation conditions is dependent on the nature of the nucleic acid substrate. Thus, in contrast to the method employed for dephosphorylation of the protruding 5' termini resulting from a "staggered" restriction enzyme cleavage, recessed 5' terminal phosphoryl groups and those at the ends of blunt or "flush-cut" nucleic acid duplexes require more drastic conditions. This takes the form of a series of brief incubations at elevated temperature, a step limited by the instability of CIP enzyme to thermal denaturation (c.f. (b) above).

As is explained in detail below, a consideration of the reaction conditions, including substrate and reagent concentrations and the mechanism of action of the phosphatases, suggests that by conducting the reaction at elevated temperatures, increase in reaction velocity is achieved. In contrast to CIP, BAP undergoes thermally induced denaturation at temperatures over 90° C., and would thus appear to permit a greater degree of flexibility in selection of optimal reaction conditions; however, the removal of the enzyme activity would then present a problem due to its increased thermal stability.

The rate-limiting step is pH dependent and is identified as either dephosphorylation of the intermediate phosphoryl enzyme (acid pH) or dissociation of $P_i$(alkaline pH). That is, the chemical event of substrate dephosphorylation is fast for either BAP or CIP. Under conditions where reagent enzyme is employed in amounts at least equivalent to substrate, the relative magnitudes of phosphatase specific activity have little effect in controlling the overall reaction rate. Thus, claims for "highest specific activity" are not fundamentally relevant to the selection of reagent.

The single major factor limiting the velocity of the phosphatase reaction is substrate (nucleic acid 5' termini) concentration. Typically, substrate concentrations are in the range of $10^{-8}M$, some three to four orders of magnitude below saturating concentrations ($K_m$ $10^{-5}M$ at pH 8.0). Under these conditions, comparison of maximal reaction velocities for enzyme from different sources does not provide a meaningful criterion for reagent selection. Indeed, current protocols call for use of a 1-5-fold molar excess of enzyme suggesting that the reaction rate is limited by the number of encounters between substrate and enzyme leading to productive binding rather than the rate of chemical conversion. At the pH of reaction, the rate limiting step in the phosphatase mechanism is $P_i$ (product) dissociation so that velocity limitation occurs after the relevant chemistry has occurred. This also suggests that successive addition of aliquots of either BAP or CIP during the course of incubation does not serve a useful purpose.

The effective BAP or CIP conentration will however be substantially reduced if significant levels of $P_i$ are present in reagents or as contaminants of reaction vessels. $P_i$ is a potent competitive inhibitor of the phosphatases ($K_I = 10^{-6}M$-$10^{-5}M$). Saturating concentrations of $P_i$ can, therefore, be introduced by use of detergent washed glassware. This can be avoided, if required, by acid-washing of laboratory glassware prior to use.

In principle, increasing the probability of an effective encounter can be accomplished by raising the reagent (BAP or CIP) or substrate concentration. To have a significant effect on the reaction velocity, enzyme concentration would have to be increased by orders of magnitude, complicating the requisite removal of activity prior to succeding reactions. Alternatively, the reaction temperature can be increased, a procedure limited by the stability of reagent enzyme and nucleic acid substrate.

However, if a suitable thermally stable enzyme is selected, thus providing an enhanced dephosphorylation step, the problem still remains as how to remove the activity so that it will not contaminate subsequent steps of the protocol.

Loss of the firmly bound metal ions (Zn(II)) of BAP results in an elimination of catalytic activity and a substantial reduction in thermal stability. Thus while at pH 8.0, the metalloprotein unfolds at temperatures above 90° C.; the metal-free apoprotein is denatured at a temperature of 57° C. (Chlebowski, J. F. and S. Mabrey, J. Biol. Chem. (1977)) 252: 7042). Metal-ion removal thus converts the active stable enzyme into an inactive form whose heat lability parallels that of the CIP enzyme. Traditional approaches to metal ion "removal" employ treatment of the enzyme with low MW chelating agents (EDTA, o-phenanthroline) or Chelex resin. "Removal" of metal ions mediated by these reagents is a passive process, dependent on the off rate of metal ion from the protein binding site. However, this redistribution of metal ion to the chelator, present in high molar excess, occurs on a time scale (hrs) sufficiently slow to be inappropriate as a modification of this procedure (Applebury, M. L. and J. E. Coleman J. Biol. Chem. 244: 308 (1969)).

It has now been surprisingly shown that BAP can be prepared in a form which can be irreversibly inactivated by metal-ion removal without requiring a subsequent heat step. On treatment with trypsin, the amino terminal decapeptide is cleaved from the mature enzyme resulting in a small decrease in specific activity but leaving the denaturation temperature substantially unaltered. On exposure to metal-ion chelators, enzymatic activity is lost and cannot be restored even on incubation with excess Zn(II). The trypsin-modified protein (tm-BAP) thus retains its activity and thermal stability until the metal-ions are disassociated.

The difference in the behavior of these reagents appears to be due to subtle structure alterations of tm-AP which are amplified on removal of the Zn(II) and Mg(II) metal ions. The examples detail calorimetric and sedimentation data which strongly indicate that the tm-AP disassociates into subunits on removal of metal ions. While such behavior also occurs, albeit at much lower protein concentrations with BAP, the native enzyme can be rapidly reconstituted into an active dimeric form in the presence of Zn(II) ion. This is not the case for tm-AP which remains monomeric and inactive even in the presence of excess Zn(II). The Zn(II) metal ion is a ubiquitious contaminant of water, buffers, glassware and reagents. Maintenace of a Zn(II)-free environment is possible, but is both tedious and expensive. Adventitious recovery of phosphatase activity is a major problem in the application of the "end-labelling" of nucleic acids with radioisotopes. The data presented indicate that tm-AP affords the advantage of an enzyme reagent whose activity can be irreversibly and rapidly eliminated.

EXAMPLE I

This example illustrates the effect of trypsin on the activity of alkaline phosphatase from E. coli as reported in J. Biol. Chem. 259 (2); 729 (1984), the contents of which are incorporated by reference.

Methods and Materials

Enzyme and Chemicals - Alkaline phosphatase was isolated from E. coli strain CW3747 (A.T.C.C. 27256) according to the method described by Applebury et al. (Applebury, M. L. et al. J. Biol. Chem. 245: 4968 (1970)). Enzyme concentrations were determined spectrophotometrically at 278 nm using $E_{1\,cm}^{0.1\%}=0.72$. Molar calculations were based on $M_r=94,000$. The enzyme activity was assayed as the rate of hydrolysis of PNPP[1] to p-nitrophenol. The reaction was monitored by following the increase in absorbance at 410 nm ($\Delta\epsilon=1.62\times10^4 M^{-1}\,cm^{-1}$) in a solution of $1\times10^{-3}M$ PNPP, 1M Tris HCl, 10 mM $MgCl_2$, $5\times10^{-5}M$ $ZnCl_2$, pH 8.0, 20° C. Apoalkaline phosphatase was prepared by dialysis against buffer containing 5 mM ortho-phenanthroline. All equipment and solution used in preparing apoalkaline phosphatase were metal free. Trypsin, PNPP, and carboxypeptidase Y were obtained from Sigma. Polybuffer 74 was obtained from Pharmacia. All other chemicals employed were reagent grade.

[1]The abbreviations used are: PNPP, p-nitrophenolphosphate; DSC, differential scanning calorimetry; Bis-Tris, 2-[bis(2-hydroxy-ethyl)amino]-2-(hydroxymethyl)-propane:1,3-diol; $T_m$, transition temperature; $\Delta h_d$, specific transition enthalpy.

Chromatofocusing - Chromatofocusing of native and trypsin-modified alkaline phosphatase was performed on a Pharmacia fast protein liquid chromatorgaphy system using a Mono P HR5/20 column and Polybuffer 74. The column was equilibrated with 0.025M Bis-Tris-HCl, pH 6.7 buffer. The protein was eluted with 0.0075 mmol/pH unit/ml Polybuffer 74, pH 5.0, at 1 ml/min in a total of 26 ml. These conditions provided a linear pH gradient from pH 6.0 to 5.0. To prepare trypsin-modified alkaline phosphatase, native alkaline phosphatase (3 mg/ml) was treated with 10% (w/w) trypsin for 60 min at 20° C. and the major protein peak was isolated using the above chromatofocusing procedure. The Polybuffer 74 was removed from the samples by chromatography on Sephadex G-75.

Differential Scanning Calorimetry (DSC) -Calorimetric measurements were made on a Microcal Mc-1 calorimeter. Reference and sample volumes of 1 ml were used. The enzyme concentration in all samples was $2.1\times10^{-5}M$. A scan rate of 1° C./min was employed with a temperature range of 25°-100° C. The calorimetric scans displayed record the differential heat capacity of the sample cell versus the reference cell as a function of temperature. The reported transition temperatures, $T_m[1]$, are the temperatures at the point of maximum amplitude for a given peak. Comparison of the area under the transition curves to standard areas generated by an applied calibration voltage allowed the determination of specific transition enthalpies ($\Delta h_d$). Areas were measured by cutting and weighing the transition curves.

Sequencing—The $NH_2$-terminal sequence was determined using both manual (Tarr. G. E., Methods Enzymol. 47: 355 (1977)) and automated Edman degradations (Peterson, D. L. et al. J. Biol. Chem. 275: 10,414 (1982)). The automated procedure was performed on a Beckman 890C Sequencer. The COOH-terminal analysis was performed using a modification of the procedure described by Hayashi (Method. Enzymol. 47: 84 (1977)). 10 nmol of protein were dissolved in 250 ul of 50 nM sodium acetate buffer, pH 5.5. 33 nmol of carboxypeptidase Y in $H_2O$ were added. The reaction mixture was made 6M in urea. Aliquots were removed at various time intervals and made 0.5N NCl. Amino acid analysis was performed on a Durrum MBF acid analyzer.

Activity Loss as a Result of Tryptic Proteolysis

The thermal stability, evaluated using differential scanning calorimetry, of alkaline phosphatase is greatly enhanced as a result of metal ion binding. The stabilizing effect of metal binding is also observed in the enzyme's proteolytic susceptibility. Apoalkaline phosphatase, enzyme from which metal ions have been removed, and native alkaline phosphatase when incubated with 10% trypsin for a total of 3 hours at either pH 6.5 or 8.0 show a loss in activity (FIG. 1). The loss in activity follows similar patterns at both pH values. Apoalkaline phosphatase rapidly loses activity; almost 75% of the initial activity is lost after a 30 minute exposure to trypsin. Essentially no activity remains after 3 hours. In contrast, approximately 20% of the activity of native alkaline phosphatase is lost after 30 minutes. No further loss is observed after 3 hours. Qualitatively similar results were obtained with pronase K (Sigma) and prolidase as the protease. When incubated with 1% trypsin (FIG. 2), native AP shows a progressive loss in activity which reaches a limiting value 75% that of the native enzyme after 4 hours. Thus, while metal ion binding prevents tryptic degradation of alkaline phosphatase, the enzyme appears to be susceptible to proteolytic modification.

EXAMPLE II

This Example describes the products of trypsin digested alkaline phosphatase.

To characterize the products produced by trypsin proteolysis of native alkaline phosphatase, protein which was treated with trypsin was analyzed on a 15% sodium dodecyl sulfate-polyacrylamide gel (King J. and U. K. Laemmli J. Mol. Biol. 62: 465 (1971). A small amount of lower molecular weight peptides and a large protein band which was very close in size to native alkaline phosphatase was observed. A similarly prepared sample eluted from a high performance liquid chromatography TSK 3000 sizing column as a large peak which was indistinguishable from native alkaline phosphatase and a small broad peak in a position characteristic of trypsin ($M_r=23,800$). These results indicate that the effect of trypsin is to produce a modified protein very similar in size to native alkaline phosphatase which has 20% less specific activity. Since native and altered alkaline phosphatase are not well resolved by these methods, it is possible that trypsin digests only 20% of the enzyme leaving intact the remaining 80%. To distinguish between these alternatives, a technique for separating the products which will do so on the basis of charge as opposed to size was chosen.

Alkaline phosphatase is reported to exist as three distinct isozymes, termed isozymes 1,2 and 3. Isozyme 1 has an Arg at the $NH_2$-terminus of both of the subunits. Isozyme 3 is missing the Arg residue and isozyme 2 is a dimer of both types of subunits (Kelly, P. M. et al. Biochem. 12: 3499 (1973). The isozymes are separated and purified using ion-exchange chromatography on Whatman DE53. FIG. 3 shows the progressive change in the products of tryptic proteolysis of native alkaline phosphatase as analyzed using chromatofocusing. Native alkaline phosphatase, which is a mixture of isozymes, separates into three distinct species (FIG. 3A). When treated with 1% trypsin (FIG. 3, B-E), a progressive increase in the peak eluting at pH 6.0 is apparent. A concomitant decrease in other protein peaks is also observed.

A plot of peak height ($A_{280}$) versus time (inset, FIG. 3) shows that the progressive increase in the peak follows a time course which parallels the loss in activity of native alkaline phosphatase when treated with 1% trypsin. Isozyme 1 co-elutes at pH 6.0 with the trypsin-produced peptide. These results indicate that the trypsin is able to act on most, if not all, of the protein present producing a single product. This species is referred to herein as trypsin-modified alkaline phosphatase.

EXAMPLE III

This Example illustrates the isolation and sequencing of trypsin-modified alkaline phosphatase.

A sample of alkaline phosphatase which did not contain isozyme 1 was used for isolating trypsin-modified alkaline phosphatase to prevent contamination by unmodified enzyme. Alkaline phosphatase was treated with 10% trypsin for 60 minutes. The trypsin-modified alkaline phosphatase produced was purified from any undigested protein or any smaller peptides and trypsin using chromatofocusing. The fraction which eluted at pH 6.0 was used for characterization of trypsin-modified alkaline phosphatase.

Results of sequence determinations of trypsin-modified alkaline phosphatase are shown in FIG. 4. The $NH_2$-terminal sequence was determined using both manual and automated Edman degradations. Both techniques show that trypsin cleaves the Arg-10 Ala-11 bond leaving Ala as the $NH_2$-terminal residue. The automated sequence determination also showed that the amino acid residue at position 15 is not Asn as previously reported, but is Asp. This is in agreement with the nucleotide sequence of the $NH_2$-terminal region of pho A, the structural gene for alkaline phosphatase. The COOH-terminal sequence of trypsin-modified alkaline phosphatase was determined using carboxypeptidase Y. This was done because there is a trypsin site at the Lys-443 Ala-444 bond which, if accessible, would result in a peptide of a size consistent with that qualitatively observed for trypsin-modified alkaline phosphatase. The results show that the COOH terminus is unchanged and matches the native sequence of Leu-Lys.

EXAMPLE IV

This example provides the characterization of the trypsin-modified alkaline phosphatase.

On an 8-20% sodium dodecyl sulfate-polyacrylamide gradient gel, a small difference in the mobility of native alkaline phosphatase and trypsin-modified alkaline phosphatase is apparent, consistent with the small molecular weight difference of the two proteins. The UV spectrum of these two forms of alkaline phosphatase are identical.

Kinetic studies comparing trypsin-modified alkaline phosphatase and native alkaline phosphatase (FIG. 5A and B) sow differences between the two forms. The $V_{max}$ for trypsin-modified alkaline phosphatase (2000 $\mu$mol/h/mg) is 22% lower than that for native alkaline phosphatase (2500 $\mu$mol/h/mg). Trypsin-modified alkaline phosphatase exhibits a higher apparent affinity for the substrate (PNPP) than native alkaline phosphatase as is reflected in the $K_m$ value which is lower for trypsin-modified alkaline phosphatase ($1.9 \times 10^{-5}$ M) than for the native enzyme ($4 \times 10^{-5}$ M. Consistent with the above result is the tighter $P_i$ binding as demonstrated by the $K_I$ for $P_i$ for trypsin-modified alkaline phosphatase which is $1 \times 10^{-5}$ M compared to a $K_I$ of $1.5 \times 10^{-5}$ M for native alkaline phosphatase. This tighter $P_i$ binding may, in part, account for the decrease in $V_{max}$ demonstrated by trypsin-modified alkaline phosphatase since $P_i$ dissociation at alkaline pH is the rate-determining step in the reaction mechanism.

DSC is a technique for monitoring the thermally induced unfolding of a protein. This method has been used previously with this enzyme system and shown to be a powerful method for assessing the stability of various alkaline phosphatase species. Since thermal stability often parallels proteolytic susceptibility, it was decided to use DSC as an additional method for characterization of trypsin-modified alkaline phosphatase. The results of DSC experiments are presented in FIG. 6. There appear to be significant differences in the thermal stability of native and trypsin-modified alkaline phosphatase. The transition temperature ($T_m{}^1$) for trypsin-modified alkaline phosphatase is 90° C. which is lower than that for apoalkaline phosphatase reconstituted with saturating Zn(II) and Mg(II) ($T_m$-93.5° C.). When 2 eq of $P_i$ are added to trypsin-modified alkaline phosphatase a shift to a more stable species is observed increasing $T_m$ to 96° C. Native alkaline phosphatase, which contains bound $P_i$ as isolated, has a $T_m$ of 98.5° C., significantly higher than the other species. The specific transition enthalpies ($\Delta h_d{}^1$) for the modified and unmodified enzyme forms are also different. The value for trypsin-modified alkaline phosphatase is the lowest (5.3 cal $g^{-1}$) and it is an apo-like value. Native and reconstituted apoenzymes have very similar enthalpies, 8.14 and 8.3 cal $g^{-1}$, respectively, in agreement with values previously reported. Addition of 2 eq of $P_i$ to trypsin-modified alkaline phosphatase causes not only a shift to a more thermally stable species, but also produces a substantial increase in $\Delta h_d$ (10.66 cal $g^{-1}$).

EXAMPLE V

This example illustrates the trypsin modification of isozyme 1 of alkaline phosphatase. As described in Example II, alkaline phosphatase exists as three distinct isozymes, termed isozymes 1, 2, and 3. Isozyme 1 has an Arg at the $NH_2$-terminus of both of the subunits, isozyme 3 is missing the Arg reside, and isozyme 2 is a dimer of both types of subunits. Characterization of the trypsin-cleaved form of the enzyme as described in Example IV was performed on the product of protease treatment of isozymes 2 and 3 since the product could not be chromatographically resolved from isozyme 1. Since this may limit the formation of the modified protein in substantial quantities, it was desirable to extend these studies to the proteolytic modification of the major protein form, isozyme 1.

Consideration of the net charge on the susceptible peptide provides an explanation for the elution of trypsin-modified alkaline phosphatase at the same pI as isozyme 1. Cleavage at the Arg-10 Ala-11 bond (the sequence of alkaline phosphatase as reported is based on the primary structure of isozyme 3) of isozyme 1 would result in release of an eleven residue peptide bearing two Arg and two Glu residues. At pH values near neutrality, the net charge of the peptide would be negligible. Thus, both isozyme 1 and the trypsin-modified protein would be expected to have comparable pI values, and therefore elute at the same pH from a chromatofocusing column. Since isozyme 1 and trypsin-modified alkaline phosphatase elute together, chromatofocusing is not useful for monitoring the trypsin reaction to form modified enzyme from isozyme 1. To verify that isozyme 1 was susceptible to the trypsin in the same way as isozymes 2 and 3, isozyme 1 was treated with 10% trypsin and the modified species was identified by amino-terminal sequencing and by SDS polyacrylamide gel electrophoresis (FIG. 12). The sequencing results show Ala-Ala as the first two amino acids, consistent with the sequence of trypsin-modified alkaline phosphatase. On a 12% SDS gel, we observe a single band which runs slightly faster than native alkaline phosphatase. A mixture of modified and native enzyme shows 2 bands on these gels, corresponding to modified and unmodified subunits. These results indicate that isozyme 1 is susceptible to trypsin as are isozymes 2 and 3.

A more convenient method for preparing larger amounts of trypsin-modified alkaline phosphatase is through the use of trypsin attached to agarose beads. This method (see Materials and Methods below) results in complete modification of native alkaline phosphatase as evidenced by chromatofocusing and SDS polyacrylamide gel electrophoresis. The reaction is stopped by removal of the trypsin agarose by filtration, thus, no column chromatography is necessary. Larger amounts of enzyme can be modified at one time and no loss or dilution occurs.

MATERIALS AND METHODS

Enzyme and Chemicals—Alkaline phosphatase was isolated from *E. coli* strain CW3747 according to the method described by Applebury et. al. supra. Enzyme concentrations were determined spectrophotometrically at 278 nm using $E^{0.1\%}_{1\ cm}=0.72$. Molar calculations were based on a MW=94,000. The enzyme activity was assayed as the rate of hydrolysis of p-nitrophenylphosphate (PNPP) to p-nitrophenol. The reaction was monitored by following the increase in absorbance at 410 nm ($\Delta\epsilon=1.62\times 10^4 M^{-1} cm^{-1}$) in a solution of $1\times 10^{-3}$M PNPP, 1M Tris-HCl, 10 mM MgCl$_2$, $5\times 10^{-5}$M ZnCl$_2$, pH 8.0, 25° C. Apoalkaline phosphatase was prepared by dialysis against buffer containing 5 mM orthophenanthroline. All equipment and solutions used in preparing apoalkaline phosphatase were metal free. Trypsin modified alkaline phosphatase was prepared by exposing native alkaline phosphatase to 10% (w/w) isolated using chromatofocusing (see below). As an alternative, modified alkaline phosphatase was prepared by treating native enzyme with trypsin attached to agarose beads in a ratio of 100 units of trypsin activity per 70 mg of protein for 3 hours, 25° C., with stirring. The reaction was stopped by filtration on Millipore filters to remove the trypsin. Trypsin, PNPP, and trypsin-agarose were obtained from Sigma Chemical Company. Spectrographically pure Zn(II) was obtained from Johnson-Matthey Chemicals, Fisher Scientific distributor. All other chemicals employed were reagent grade.

Calorimetric measurements were made on a Microcal MC-1 calorimeter. Reference and sample volumes of 1 ml were used. The enzyme concentration in all samples was $2.1\times 10^{-5}$M. These samples were vacuum degassed prior to loading in the calorimeter and the cells were thoroughly flushed with 5 mM EDTA and metal-free water to remove trace contaminants of metal ions prior to use. A scan rate 1° C. min$^{-1}$ was employed with a temperature range of 25°–100° C. The calorimetric scans displayed record the differential heat capacity of the sample cell vs. the reference cell as a function of temperature. Comparison of the area under the curves to standard areas generated by an applied calibration voltage allowed the determination of specific transition enthalpies ($\Delta h_d$). Areas were measured by cutting and weighing the transition curves. The reported transition temperatures ($T_m$) are the temperatures at the point of maximum amplitude for a given peak.

An excitation (291 nm) and emission (331 nm) spectrum for native and trypsin-modified alkaline phosphatase were generated using an SLM 4000/4000S polarization spectrofluorometer.

SDS polyacrylamide gel electrophoresis was performed using the method of King and Laemmli (supra). A 12% separating gel at pH 8.8 and a 4.5% stacking gel at pH 6.8 were employed. The samples were prepared by addition of an equal volume of sample buffer (0.125 M Tris-HCl, 0.15 M SDS, 20% glycerol, 1.43 M β-mercaptoethanol, pH 6.8) to 5–10 ug of protein and heating in a boiling water bath for 5 minutes. Electrophoresis was carried out at 35 milliamps, constant current, until the dye marker (bromophenol blue) ran off the bottom of the gel (about 5 hours). The apparatus used was a Bio Rad Protean cell which was cooled with tap water. The electrode buffer consisted of 0.025 M Tris, 0.2 M glycine, and 0.3.7 mM SDS, pH 8.3. The gel was stained overnight in a 0.25% Coomassie Blue R250 Stain and destained for 6 hours.

The NH$_2$-terminal sequence was determined using automated Edman degradations (supra). The procedure was performed on a Beckman 890C sequencer.

Chromatofocusing of native and trypsin modified-alkaline phosphatase was performed on a Pharmacia fast protein liquid chromatography system using a Mono P HR5/20 column and Polybuffer 74. The column was equilibrated with 0.025 M Bis-Tris-HCl, pH 6.7 buffer. The protein was eluted with 0.0075 mmol/pH unit/ml Polybuffer 74, pH 5.0, at 1 ml min$^{-1}$ in a total of 26 ml. These conditions provided a linear pH gradient from pH 6.0 to 5.0.

The UV Spectra of native, apo, trypsin-modified and apotrypsin modified alkaline phosphatase were generated using a Varian Cary 210 Spectrophotometer scanning from 350 to 240 mm.

The Zn(II) binding to alkaline phosphatase was determined using an IL Video 22 AA/AE spectrophotometer. 2 ml samples at 1.34 mg/ml, containing saturating concentrations of Zn(II) and Mg(II) ($5\times 10^{-5}$M ZnCl$_2$, 10 mM MgCl$_2$) were dialyzed against 2L of metal free buffer, 0.01 M Tris, 0.01 M NaOAc, 0.1 M NaCl, pH 8.0 and buffer containing 10 mM MgCl$_2$ for 24 hours at 20° C. Samples were diluted 1 to 30 and the Zn(II) content was measured using the flame mode of the AA.

Sedimentation velocity experiments were performed in a Beckman model E analytical ultracentrifuge. Samples were 2.5 mg ml$^{-1}$ in 0.01 M Tris, 0.01 M NaOAc, 0.1 M NaCl, pH 8.0 buffer. The apotrypsin modified enzyme sample contained 10% (w/w) soybean trypsin inhibitor to prevent any proteolysis by trypsin contamination. The instrument was equipped with a Schlieren optical system. An An-D rotor was employed at a speed of 56,000 RPM, 20° C.

METAL ION ASSOCIATION AND DIMER INTEGRITY

Previous Examples demonstrate that trypsin-modified alkaline phosphatase is significantly different from the native enzyme in its kinetic and thermodynamic properties. These differences do not appear to be related to substantial alterations in the environment of aromatic amino acids since the ultraviolet and fluorescence spectra (excitation wavelength of 291 mn) for the native and modified enzyme were virtually identical. Since the metal ions of the enzyme are required for structural stabilization and activity, a comparison of the Zn(II) binding of the native and modified enzyme was performed using atomic absorption spectroscopy. In the presence of saturating (i.e. 10 mM) concentrations of Mg(II), both enzyme species firmly bind four equivalents of Zn(II). When native enzyme, exposed to saturating concentrations of Zn(II) and Mg(II), is dialyzed exhaustively against metal-free buffer, 6 equivalents of Zn(II) bind to the protein in agreement with prior reports (Coleman, J. E. et al., *J. Biol. Chem.* 258: 386 (1983)). In contrast, the trypsin-modified enzyme binds but four equivalents of Zn(II) under the same conditions suggesting an alteration in the metal-binding locus of the enzyme.

The consequences of this apparently modest structural change are amplified when the properties of the metal-free apoproteins are compared. Apotrypsin-modified alkaline phosphatase was prepared using the same technique as that routinely used to prepare apoalkaline phosphatase from the native enzyme. As is the case for the native enzyme, the modified apoprotein is devoid of catalytic activity. It is possible to reconstitute essentially 100% activity by addition of saturating concentrations of Zn(II) and Mg(II) to apoalkaline phosphatase (specific activity = 3000 $\mu$mole hr$^{-1}$ mg$^{-1}$). In contrast, addition of these metals to apotrypsin-modified alkaline phosphatase does not reconstitute activity (specific activity = 45 $\mu$mole hr$^{-1}$ mg$^{-1}$).

A structural basis for this loss of Zn(II) dependent activity emerged from studies of the apomodified enzyme using differential scanning calorimetry and velocity sedimentation. The calorimetric scan of the apomodified protein has a transition temperature ($T_m$) of 42° C. (FIG. 7). The apo-form of native phosphatase has a transition temperature at pH 8.0 of 57° C. (FIG. 7 inset). Addition of 2 equivalents of Zn(II) to apoalkaline phosphatase results in a large stabilization and a shift in $T_m$ to 90° C. In contrast, addition of 2, 4, or 6 equivalents of Zn(II) to the apomodified enzyme results in only a small change in $T_m$ which is shifted to 46° C. The transition enthalpy ($\Delta h_d$) for the apomodified protein (1.4 cal g$^{-1}$) is low in comparison to that observed for the native apoenzyme (5.3 cal g$^{-1}$) and is raised only slightly on addition of Zn(II) ($\Delta h_d$=2.3 cal g$^{-1}$) in contrast to the effect of Zn(II) addition to the native apoprotein which raises the transition enthalpy to a value of 8.0 cal g$^{-1}$. The calorimetric parameters observed for the apomodified protein are strikingly similar to those observed for the monomeric form of the native enzyme (generated by formamide treatment of the apoprotein dimer) which displays values of $T_m$=37° C. and $\Delta h_d$=1.9 cal g$^{-1}$ under similar conditions (Chlebowski, J. F. et al., *J. Biol. Chem.* 254: 5745 (1979)).

Results of sedimentation velocity experiments demonstrate that while native apophosphatase, and trypsin-modified phosphatase run as similarly shaped and size molecules (S=5.8), apomodified phosphatase is quite different. The sedimentation coefficient observed for the apomodified protein (S=3.3) is comparable to those previously observed for the monomeric form of the enzyme, which range from 2.3 to 4.0. These observations indicate that the removal of metal ions from the modified enzyme results in an alteration and reduction in the intersubunit affinity resulting in a dissociation of subunits at protein concentrations greater than 10$^{-5}$M. While the calorimetric data suggest that the monomer species retains an affinity for Zn(II), metal ion binding fails to drive dimer formation and the restoration of catalytic activity as is the case for the native enzyme (See FIG. 8).

As shown in FIG. 7, the binding of two Zn(II) ions at pH 8.0 appears to account for the major degree of thermal stabilization afforded to the apoprotein. This suggests that the structural reorganization of the enzyme is essentially complete at substoichiometric ratios of bound metal ion. However, trypsin modification differentially affects the native, apo and 2Zn(II) forms of the enzyme (FIG. 8). As previously shown, a 20% loss in activity is observed for the native enzyme compared to 100% for the apoenzyme on treatment with 10% trypsin (FIG. 8). In contrast, 2 eq of Zn(II) gives the enzyme an intermediate protection yielding a product with 60% of the activity of the native protein.

HYBRID DIMER FORMATION

As described above, the chromatographic mobility of the trypsin modified enzyme can be explained on the basis of alterations in the net charge of the protein taking into account only the deletion of charged residues in the amino-terminal peptide. The progressive changes in structure and chromatographic mobility for the three isozyme forms of the protein suggested by this explanation are depicted in FIG. 9. If the progressive cleavage depicted does in fact occur, this suggested that it might be possible to intercept the half-modified form of the enzyme (i.e. a dimer of modified and unmodified subunits) on trypsin cleavage of isozyme 3. A sample composed of isozyme 2 and 3 only was treated with 1% trypsin and shows an increase in the peak eluting at pH 5.9 (the position is isozyme 2) before it decreased (FIG. 10). Samples were removed at the indicated times and analyzed using chromatofocusing. A progressive increase in the peak eluting at pH 6.0 (trypsin-modified alkaline phosphatase) is observed as expected. The peak eluting at pH 5.9 corresponds to isozyme 2 and also to half-modified form before it is completely modified. A sample of alkaline phosphatase composed of 75% isozyme 3 and 25% isozyme 2 was treated with trypsin agarose (1.6 units per mg alkaline phosphatase$^{-1}$) and at various times the reaction was stopped by filtration and the products were analyzed using chromatofocusing. The areas of the peaks eluting at the positions of the 3 isozymes were integrated (using an HP3390A integrator) and percent composition of the total area was plotted as a function of the time of exposure to the trypsin (FIG. 11A). These data confirm the formation of the half-modified form of isozyme 3. The curve corresponding to the peak eluting at pH 5.9 shows an increase in that peak area before decreasing. The curves for the peaks eluting at pH 6.0 (isozyme 1 and trypsin-modified alkaline phosphatase) and pH 5.8 (isozyme 3) increase and decrease respectively as expected. A sample composed of isozyme 2 (FIG. 11B) and treated with trypsin does not show the increase in the area of the peak eluting at pH 5.9. These results indicate that production of large amounts of isozyme 3 will allow isolation of the half-modified form for studies related to subunit-subunit interactions and half sites reactivity. The three species, isozyme 3, trypsin-modified alkaline phosphatase, and the half-modified protein are separable on the basis of charge.

EXAMPLE VI

This example demonstrates that tm-AP does function as an effective reagent in dephosphorylating DNA and 2) tm-AP can be rapidly and irreversibly inactivated on exposure to metal ion chelating agents, in contrast to the available enzyme reagent. Experimental procedures for the data shown in FIGS. 13 and 14 are given as Figure legends.

Shown in FIG. 13 is the time course of the labilization of radiolabel ($^{32}P$ as terminal nucleic acid phosphoryl group) on treatment of DNA with calf intestinal alkaline phosphatase, CIP, (open circles) or the trypsin-modified enzyme, tm-AP (closed circles). The data are presented as the percent of label are retained on filters as a function of the duration of phosphatase treatment. Labilized phosphate is washed through the filter in this procedure. Thus a decrease in radioactivity indicates successful dephosphorylation of the DNA by the enzymatic reagent. Both CIP and tm-AP dephosphorylate the nucleic acid; furthermore these is no difference (within experimental error) in the efficiency with which this process occurs for the two enzymes. Thus it is clearly shown that the trypsin modified bacterial alkaline phosphatase dephosphorylates the termini of nucleic acids with an efficiency equal to that of the alternative enzymatic reagents CIP or BAP.

Shown in FIG. 14 is the time course of inactivation of tm-AP and the native bacterial alkaline phosphatase, BAP, on exposure to ethylene diamine tetraacetic acid (EDTA), a metal-ion chelating agent. The tm-AP (closed circles) loses activity at a rate two to three times that observed for the native enzyme (open circles). Thus while the activity of tm-AP is reduced to zero in 1.5 hours under these conditions, inactivation of BAP requires 3.5 hours. Following inactivation, samples of the enzymes were dialyzed against buffer solutions containing Zn(II) and Mg(II) ions (arrow in FIG. 14). Under these conditions BAP recovers 70%–100% of its original activity; in contrast, tm-AP remains inactive. These data show that the trypsin-modified enzyme is rapidly inactivated on exposure to EDTA; the rate of inactivation exceeds that observed for the bacterial alkaline phosphatase; and inactivation of tm-AP is irreversible, in contrast to BAP.

What is claimed is:

1. A proteolytically modified alkaline phosphatase wherein said modification results in the removal of a polypeptide fragment from the NH$_2$ terminus of said phosphatase and wherein said polypeptide fragment contains 10 or 11 amino acids and wherein said phosphatase has been proteolytically modified by a protease selected from the group consisting of pronase K, and prolidase.

2. The phosphatase according to claim 1 wherein the phosphatase is isolated from a bacteria.

3. The phosphatase according to claim 4 wherein said bacteria is *Escherichia coli*.

4. The phosphatase according to claim 3 wherein said fragment has the amino acid sequence +NH$_2$—(R)$_n$T PEMPVLENR—COO—, wherein n is 0 or 1.

5. A trypsin modified bacterial alkaline phosphatase characterized in having 10 or 11 amino acids deleted from the NH$_2$ terminal region thereof when compared to the native unmodified enzyme, having dephosphorylating activity of up to about 80% of the native unmodified enzyme and capable of substantially total irreversible inactivation upon removal of divalent ions.

6. A process for the production of a proteolytically modified alkaline phosphatase comprising contacting a native alkaline phosphatase with a proteolytic enzyme selected from the group consisting of pronase K and prolidase in a reaction mixture under conditions of time and temperature sufficient to result in the removal of an NH$_2$ terminal fragment having 10 or 11 amino acids.

7. The process according to claim 6 wherein said phosphatase is isolated from *Escherichia coli*.

8. The process according to claim 6 wherein said pronase K or prolidase is present in an amount of about 10% (w/w) and is reacted with native alkaline phosphatase at about 20° C. for about 60 minutes.

9. The process according to claim 6 wherein said pronase K or prolidase is immobilized.

10. The process according to claim 9 wherein said pronase K is prolidase is immobilized on agarose beads and is reacted with native alkaline phosphatase in a ratio for about 100 units of trypsin activity per 70 mg of protein for about 3 hours at about 25° C.

11. In a method for enzymatically dephosphorylating the 5' phosphate groups of nucleic acids, the improvement which comprises contacting the nucleic acid to be dephosphorylated under dephosphorylating conditions with a proteolytically modified alkaline phosphatase wherein said modification results in the removal of a polypeptide fragment from the NH$_2$ terminus of said phosphatase and wherein said polypeptide fragment contains 10 or 11 amino acids and wherein said phosphatase has been proteolytically modified by a protease selected from the group consisting of pronase K, and prolidase.

12. In a method for the detection of an immunological reaction by an enzyme linked immunoassay the improvement which comprises employing a modified alkaline phosphatase as an enzymatic detection means wherein said modification results in the removal of a polypeptide fragment from the NH$_2$ terminus of said phosphatase and wherein said polypeptide fragment contains 10 or 11 amino acids and wherein said phosphatase has been proteolytically modified by a protease selected from the group consisting of pronase K, and prolidase.

13. In a method for the enzymatic hydrolysis of phosphate monoesters the improvement which comprises contacting said phosphate monoesters under hydrolysis conditions sufficient to release phosphate therefrom with a modified alkaline phosphatase wherein said modification results in the reoval of a polypeptide fragment from the NH$_2$ terminus of said phosphatase and wherein said polypeptide fragment contains 10 or 11 amino acids and wherein said phosphatase has been proteolytically modified by a protease selected from the group consisting of pronase K, and prolidase.

14. The method according to claim 12 wherein said phosphate monoester is a phosphorylated protein.

* * * * *

UNITED STATES PATENT AND TRADEMARK OFFICE
CERTIFICATE OF CORRECTION

PATENT NO. : 4,656,128
DATED : April 7, 1987
INVENTOR(S) : Jan F. Chlebowski

It is certified that error appears in the above-identified patent and that said Letters Patent is hereby corrected as shown below:

Column 13, lines 45-46: "10% (w/w) isolated using" should read as --10% (w/w) trypsin for 60 minutes at 20°C. The major protein peak was isolated using--

Column 17, line 62: "trypsin" should read as --proteolytically--

Column 18, line 5: "ions" should read as --ions wherein said phosphatase has been proteolytically modified by a protease selected from the group consisting of pronase K, and prolidase--

UNITED STATES PATENT AND TRADEMARK OFFICE
CERTIFICATE OF CORRECTION

PATENT NO. : 4,656, 128
DATED : April 7, 1987
INVENTOR(S) : Jan F. Chlebowski

It is certified that error appears in the above-identified patent and that said Letters Patent is hereby corrected as shown below:

Column 18, line 22: "is" should read as --or--

Column 18, line 24: "trypsin" should read as --pronase K or prolidase--

Signed and Sealed this

Twenty-first Day of June, 1988

Attest:

DONALD J. QUIGG

Attesting Officer      Commissioner of Patents and Trademarks